United States Patent [19] [11] 4,051,867
Forberg [45] Oct. 4, 1977

[54] MULTITUBE VALVE
[75] Inventor: Hans-Jürgen Forberg, Lensahn, Holst., Germany
[73] Assignee: Transcodan, Sven Husted-Andersen, Germany
[21] Appl. No.: 662,591
[22] Filed: Mar. 1, 1976
[30] Foreign Application Priority Data
Mar. 5, 1975 Germany .............................. 2509485
[51] Int. Cl.² ............................................. F16L 55/14
[52] U.S. Cl. ......................................... 137/595; 251/6
[58] Field of Search ........................ 137/595; 251/4, 6
[56] References Cited
U.S. PATENT DOCUMENTS

| | | | |
|---|---|---|---|
| 3,316,935 | 5/1967 | Kaiser et al. | 137/595 |
| 3,411,534 | 11/1968 | Rose | 137/595 |
| 3,533,439 | 10/1970 | Hall | 137/595 |
| 3,685,787 | 8/1972 | Adelberg | 251/6 |

Primary Examiner—Alan Cohan
Assistant Examiner—Gerald A. Michalsky
Attorney, Agent, or Firm—McGlew and Tuttle

[57] ABSTRACT

A multitube valve comprises a housing which has open front and rear ends with a plurality of channels defined between the front and rear ends each of a size to receive an individual tube therein and each including a support surface for the tube. A clamp in the form of a rotatable clamp roller has a journal extending outwardly from each side and it is engaged within respective clamp roller grooves which are defined in the housing on each side of the tube channels. The roller is movable by rotation along the grooves toward either the front or rear ends of the housing and it is of a size such that it cooperates with the support surface to compress the tubes therebetween and to at least partially close off the tubes when it is aligned over the support surface. The support surfaces are offset from each other in the longitudinal direction of the channels so that they operate at a separate time in respect to the positioning of the clamp for closing off the tube flow.

11 Claims, 11 Drawing Figures

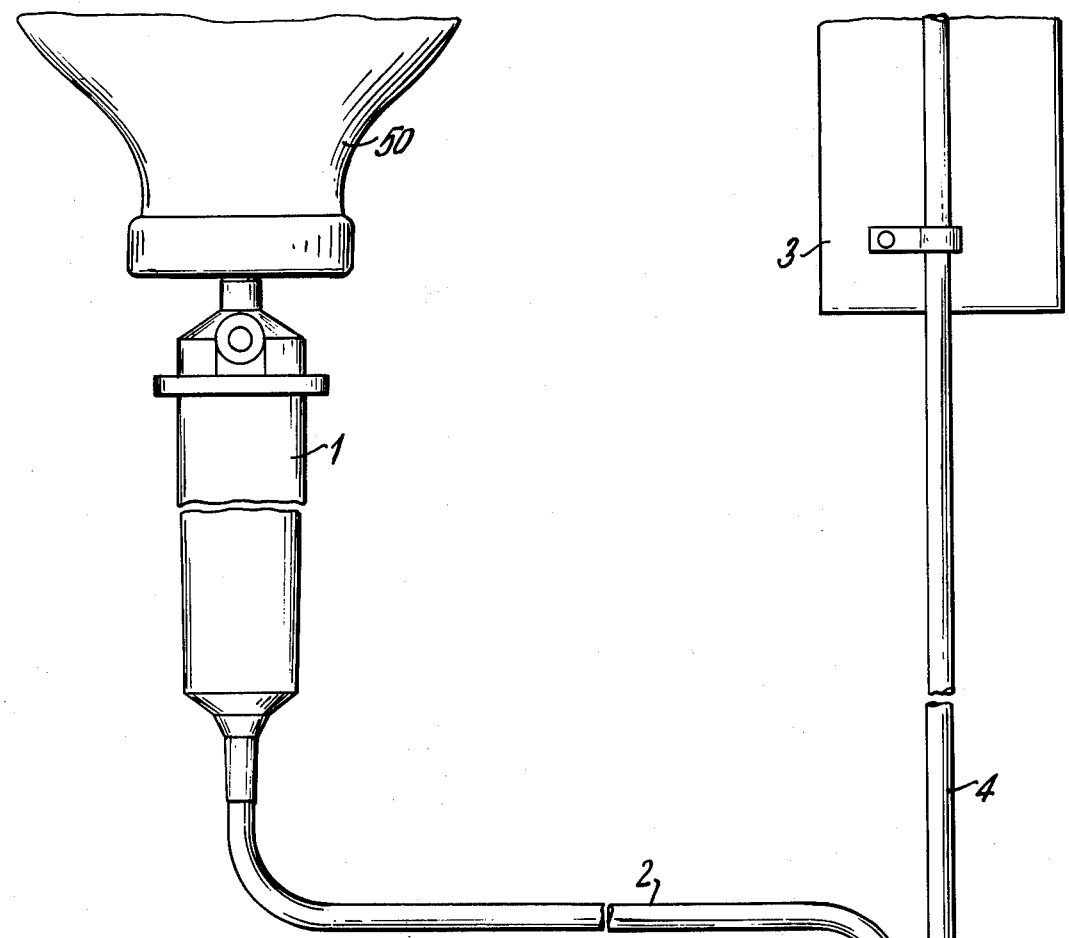
FIG. 1
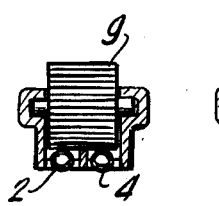 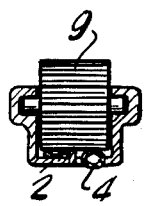 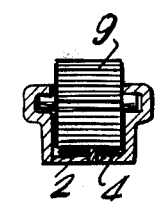 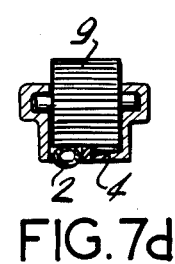
FIG.7a  FIG.7b  FIG.7c  FIG.7d

MULTITUBE VALVE

BACKGROUND OF THE INVENTION

1. Field of the Invention

This invention relates in general to the construction of valves and in particular to a new and useful multitube valve for medical, chemical or similar devices equipped with flexible tubes particularly for infusion or transfusion apparatus.

2. Description of the Prior Art

In the medical and chemical fields multiflow valves are known which are designed as plug valves. Such valves are used for example in connection with catheters which are to be introduced into a patient and which serve to selectively connect different devices such as a dropping chamber, a blood pressure connection and similar devices to the patient. A multiway valve may for example be connected to a blood removing apparatus so that the catheter is used not only for measuring the blood pressure and introducing solutions into the blood stream but also for drawing blood. Multiway valves are also needed for other purposes in the medical field for example in chemical or physical laboratories for handling the fluid substances. Such multipassage valves may be made of various materials such as metals, plastics, etc. For example a known multiway valve is designed as a plug valve having a housing of a plastic such as a polypropylene and a plug which is made of a rubber suitable for blood. With the known multiway valves in the form of plug valves, cocks or similar devices there is a risk of damaging the blood components since depending on its position the movable body of the valve projects into the cross section of the flow passages. Thus the baffle surfaces are formed and the flow through the conduits is not smooth. This may lead for example to a damage of the blood components. A further risk is that a possible leakage of such a multiway valve may take place when the plug is displaced. The sterilization must be carefully carried out particularly if such a multiway valve has to be used repeatedly. The manufacture of such valves requires a relatively great precision of the assembled component parts since they are relatively complicated. During handling, care is to be taken to keep the individual component parts movable relative to each other. Unsatisfactory tightness and leakage in medical devices is dangerous because of the possible contamination or embolism which may be associated therewith.

SUMMARY OF THE INVENTION

In accordance with the present invention, the drawbacks of the designs of known multiway valves is overcome and the invention provides a multiway valve which is of simple construction and inexpensive to manufacture so that it will be possible to use the valve as a throw-away device. In addition the valve may be operated in a very simple manner. The risk of leakage is completely eliminated both for over and under pressures. The construction is such that the valve may be easily sterilized and maintained sterile and the flow through the valve remains in separate tubes which are not dammed or baffled in any respect so that a smooth flow is effected.

In accordance with the invention the valve is designed as a valve clamp having a housing with front and rear opened ends and with a plurality of longitudinally extending substantially parallel channels defined between the front and rear ends of a size to accommodate individual flexible tubes. Each channel includes at least one tube support surface on which a flow tube may be supported with at least a portion of the space between the front and rear end left open or provided with a recess so that the tubes may be deflected below this support surface. In addition the valve clamp includes a clamping member in the form of a rotatable clamp which is supported on its own journals which extend into guidways defined on each side of the housing so that the periphery of the clamp rollers may move over the support surface in close proximity thereto so as to compress a tube supported thereon and at least partially shut off the flow therethrough. Support surfaces of the channels are advantageously offset in a longitudinal direction so that when the clamping member is moved either toward the front or rear of the housing it will be positioned over at least a portion of one of the support surfaces at a different time from the other so that the tubes in some of the channels will be shut off at a different time from the tubes of the other channels.

A feature of the inventive construction is that the fluid is conveyed only through its own flexible tube and each tube is closed either partially or fully by pinching or squeezing off the tube by the movement of the clamping member in the housing. There is thus no possibility of leakage and no possibility of contamination of the fluid since its flow through its own tube is controlled by controlling the diameter of the flow passage of the tube by compressing the tube or relieving it. Thus no difficulties arise in respect to sterilization of the whole device since the flexible tubes may be easily sterilized during manufacture and maintained in a sterilized condition. There are no baffle surfaces which may be contaminated and in fact no surfaces which become exposed to any of the operating parts. The design and manufacture of such valves is extremely simple. In practice the valve comprises only flexible tubes which can be thrown away after use and a housing with a clamping means which may be used over and over again and without contaminating the fluid in the tubes. The housing and the clamping means may be made of an inexpensive plastic material which may be formed for example by injection molding. Because the housing does not come into contact with the fluid there is no requirement that it be made of any special material which might have any particular chemical or mechanical resistance.

In accordance with a feature of the invention the clamp housing comprises a housing which advantageously has an open top and which includes a plurality for example two side by side channels which extend from the front to the rear end thereof. The clamping means which cooperates with a fixed bottom tube support surface defined in each channel is advantageously in the form of a roller having journals extending outwardly from each side which engage in grooves which run along each side of the housing over the tube support surface. The groove is shaped so that the roller will be brought into proximity above the support surface and pinch any tube supported thereon when it is located over the support surface so as to at least partially or fully close off the flow therethrough in accordance with design requirements. The guide grooves for the rollers may advantageously comprise a straight groove which extends parallel to the support surface or one which is inclined to bring the roller closer to the surface so as to effect all degrees of compression of the tube. In addition the support surface may include a recess therein at one location along its length or at a plurality of such locations which permit a partial escape of the flexible tube therein so as to provide a fine regulation of the close off of the flow when the clamping element presses the tube into such a channel. In addition the support surfaces of adjacent channels or at least one support surface in a plurality of channels is offset in the longitudinal direction from the others so that when the clamping roller is over the support surface in one channel it will not be over another so that one tube may be opened when another is closed. The housing is constructed so that at the places where there is no support surface the tube may be deflected downwardly by the passage of the clamping roller over it. For this purpose the housing may be opened downwardly or provided with a large recess to permit accommodation of the tube without compressing it to the point where it will limit or close off the flow thereof.

Thus the device may be formed with a plurality of clamping surface areas and a movable clamp member which is movable selectively over these areas in order to effect the desired clamping of each tube. Alternatively, each of the support surfaces may be provided with its own recess so that movement of the clamping member over the support surface will deflect the tube into the recess. The recesses may be made with a gradually diminishing or increasing width so that the deflection and the clamping will effect a gradual closing off or opening of the flow passage through the tube as desired. In addition the recesses in the support surface may have elevational changes therein so as to gradually or gradually close the tube flow passage which is compressed thereover by a clamping member. The device can function as a control clamp flow regulator by a construction of the support surfaces or grooves in the support surfaces or the movement of the clamping member in order to effect gradual or rapid close off of the tube or opening thereof as desired. The construction of the housing may be made particularly simple if the clamping surface or tube support surface is made parallel to the guide surface for the clamping roller. The clamping means may comprise a roller or other movable member which may be moved over the support surface for the tube and which may be positioned so that when it is over the support surface it causes a compression of the tube and a restriction of the flow. When a clamping is employed it is advantageous to make the surface of the clamping roller serrated so that it may grip easily on the tube and may be rolled thereover.

Accordingly it is an object of the invention to provide an improved device for clamping a plurality of tubes and for regulating the flow through the tubes which comprises a housing having front and rear ends with a plurality of tube channels extending from the front to the rear ends and with each channel including a support surface for receiving a tube thereon and at least a portion which permits the tube to be deflected below the support surface and which also includes a clamp which is guided for movement in the housing above any tube position in the channel so that it can be moved over each support surface to compress the tube and to constrict the flow therethrough or to completely shut off the tube flow and which advantageously includes support surfaces which are offset in a longitudinal direction in respect to at least some of the channels so that the control of the flow of each channel may be effected separately and in a different manner from the other.

A further object of the invention is to provide a device for controlling the flow through a plurality of tubes which includes separate channels in a housing for receiving the tube and with clamping means which are movable over the channels to compress any tube positions therein onto a support surface for selectively controlling the flow through the tubes by varying the area therethrough at the location of the clamping member.

A further object of the invention is to provide a clamping device and a valve control device for a plurality of fluid flows which is simple in design, rugged in construction and economical to manufacture.

For an understanding of the principles of the invention, reference is made to the following description of typical embodiments thereof as illustrated in the accompanying drawings.

BRIEF DESCRIPTION OF THE DRAWINGS

In the Drawings:

FIG. 1 is an elevational view of a blood transfusion blood pressure follower having a flow regulating device constructed in accordance with the invention;

FIGS. 7a, 7b, 7c and 7d are sectional views of the clamping device on a reduced scale taken along the lines A—A, B—B, C—C, and D—D respectively.

GENERAL DESCRIPTION OF THE PREFERRED EMBODIMENTS

Figure 6:
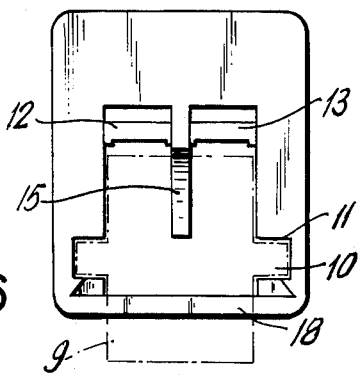
FIG. 6 is a front elevational view of the clamp housing shown in FIG. 2.
Figure 3:
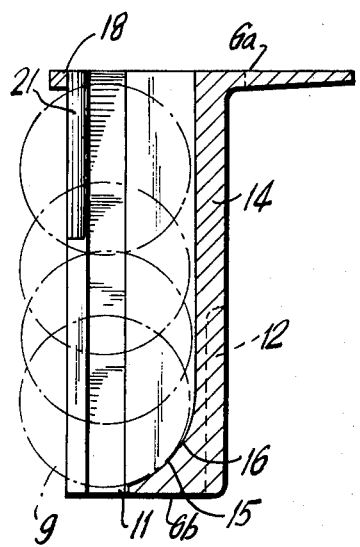
FIG. 3 is a section taken along the line III—III of FIG. 2.

Referring to the drawings in particular the invention embodied therein comprises a transfusion device for an infusion apparatus which includes a supply container 50 connected to a drop chamber 1 which in turn is connected to a flexible tube 2 for the passage of a fluid through a multitube clamp or multitube valve generally designated 52 which is constructed in accordance with the invention. In the embodiment indicated another tube 4 leading from a blood pressure follower 3 extends through the multitube clamp 52 and each tube 2 and 4 is connected to a Y-piece 7 to a tube 8 which leads to a catheter (not shown).

In accordance with the invention the multitube clamp 52 includes a housing 6 which has an open front or upstream and 6a and an open downstream or rear end 6b and which is provided with a plurality of channels, in this instance two channels 54 and 56 which extend in substantially parallel relationship from the front end 6a to the rear end 6b. The front end 6a is partially closed by a front wall 18 which extends across the top of the housing 6. Clamping means in the form of a clamping roller 9 is mounted for longitudinal displacement in side grooves 11 and 11' by means of trunnions 10 and 10' defined on each side thereof. In the embodiment indicated the guide grooves 11 and 11' are made substantially parallel to clamping surfaces 12 and 13 in respective channels 54 and 56 but the guide grooves 11 and 11' may be made at an angle to this channel in order to move a periphery 9a of the roller 9 selectively toward or away from the clamping surfaces 12 and 13 defined in the respective channels 54 and 56. A plurality of channels in a number greater than two may be provided and in each case a web 14 separates the channels. The channels extend substantially parallel and provide guideways for the tubes which are to be extended therethrough and in this case this includes flexible tube 2 and flexible tube 4. The housing includes an extension 15 at the rear end 6b which extends upwardly from the respective support surface level to the grooves 11 and which defines a curved stop surface 16 for retaining the clamping roller 9 in the housing against withdrawal. The front wall 18 at the opposite side also prevents the withdrawal of the clamping roller in this direction.

Figure 2:
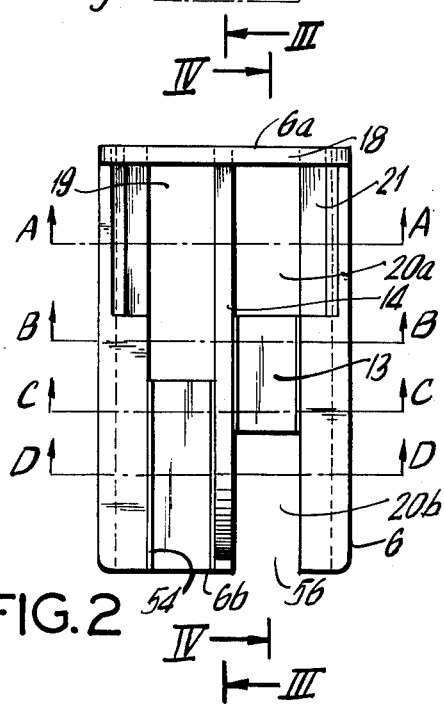
FIG. 2 is a top plan view of the clamping device shown in FIG. 1 with the clamping member removed.
Figure 4:
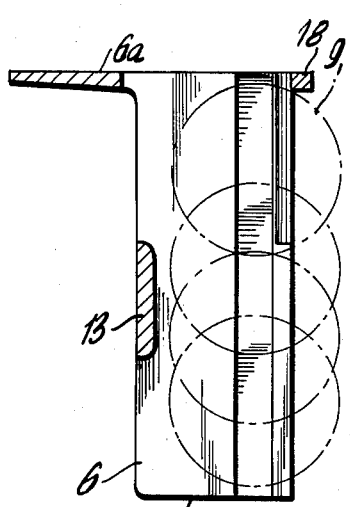
FIG. 4 is a section taken along the line IV—IV of FIG. 2.
Figure 5:
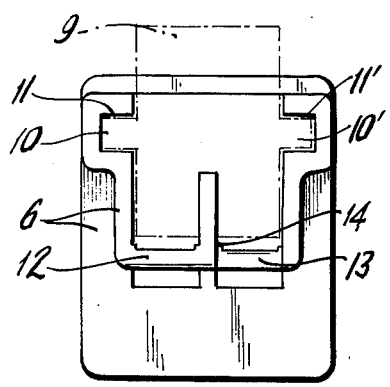
FIG. 5 is a rear elevational view of the clamp housing shown in FIG. 2.

In accordance with a feature of the invention the clamping surface 12 extends over only a portion of the length of the housing 6 and there is at least another portion which is provided with a recess or an opening such as the opening 19 which permits the tubes to be flexed downwardly beyond the level of the clamping surface 12. The clamping surface 13 extends only over the middle portion of the housing 6 and the remaining portion of the length of the channel 56 is provided with recesses or openings 20a and 20b at respective ends of the support surface 13 for the tubes and these permit downward flexing of the tubes at locations other than the support surface by the clamping roller when it is positioned over the tube at such locations. The construction is such that the tube will be clamped and the flow at least partially shut off when the clamping roller is positioned to overlie the respective tube support surfaces 12 or 13. The clamping member may be inserted in the housing through a cut-out 21 provided at the top thereof. In the mounting of the transportion roller 9 it is placed into the housing at the location A—A as shown in FIG. 2. In this position no clamping surface is opposed to the roller so that both the tubes 2 and 4 may be deflected downwardly in the respective openings 19 or 20a.

When the clamping roller A is inserted into the housing 6 at the location of the plane A—A no clamping surface is opposed to the roller so that the tubes 2 and 4 may pass therethrough and be pressed downwardly into the opening or recess 19 and 20a without causing any compression of the tube or change of the flow area. This condition is shown in FIG. 7a.

In the position of the plane B—B the clamping roller 9 is positioned so that its periphery 9a pressed the tube 4 against the clamping surface 13 so as to close off the flow area of the tube 4 and completely shutting this tube off. When the clamping roller is in the position of the plane C—C both tubes 2 and 4 are pressed against the respective support surfaces 12 and 13 and shut off preferably completely. In the position in the plane D—D only the tube 2 is compressed by the clamping surface 9a against the support surface 12 and the tube 4 is fully opened since it overlies the opening or recess 20d.

The clamping means is in the form of a roller 9 but it may also comprise a slider or similar clamping element. The housing is designed so that the channels 54 and 56 receive a single tube and only two channels are provided. The channels may of course receive a plurality of tubes or there may be a number of channels comparable to the number of tubes and this may be in excess of two.

In the embodiment indicated the support surface or the clamping surface 12 is a planar surface over its entire length and this surface is parallel to guide grooves 11 and 11' so that the entire length of the surface is uniformly spaced from the grooves and the clamping which is effected by the clamping roller during its movement over the surface will be uniform throughout the length of the surface. In the embodiment indicated this spacing is such that the tube 2 will be completely shut off and will remain closed during the passage of the clamping roller 9 over the entire length of the surface 12.

Figure 8:
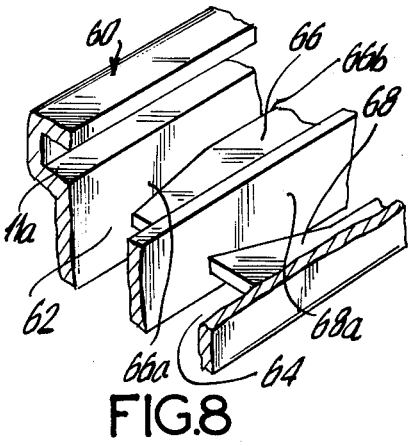
FIG. 8 is a partial front top perspective and partial sectional view of another embodiment of clamp housing.

As shown in FIG. 8 a housing 60 may comprise channels 62 and 64 having clamping surfaces or support surfaces 66 and 68 which may be aligned laterally or offset as desired. The clamping surface 66 is provided with a groove or recess 66a which provides a space for accommodating the tube when it is compressed by a clamping member similar to the clamping roller 9 in the other embodiment. The recess 66a is shaped so that there is a gradual reduction in the width as well as the height of the recess 66a to effect a gradual change of the flow area of the tube which is compressed thereover by the clamping roller. The groove 66a narrows toward the front of the housing so that there is a gradual closing offf until a complete closing off is effected when the clamping member is over the remaining surface 66b. In the channel 64 on the other hand the groove 68a widens in a direction toward the front of the housing so that there is a gradual increase in the flow rate through any tube position thereover when the clamping member is moved therealong. In this manner the clamping roller may be moved along its associated control groove 11a to effect a gradual throttling of the flow and hence a complete control of the flow in accordance with which direction movement is effected and any design arrangement to produce a desired flow change may be effected by corresponding changes of the grooves of the support surfaces for the tubes.

While specific embodiments of the invention have been shown and described in detail to illustrate the application of the principles of the invention, it will be understood that the invention may be embodied otherwise without departing from such principles.

What is claimed is:

1. A multiway valve for medical devices, chemical devices, etc. comprising a housing having an open front end and an open rear end, a plurality of tube channels defined between said front and rear ends through which individual tubes are adapted to be passed, each tube channel having a bottom tube support surface extending at least a portion of the distance between said front and rear ends and each having a second portion of the distance between said front and rear ends without a tube support surface so that the tube in the associated channel may be deflected below the level of said tube support surface, a clamp member movably mounted in said housing for movement backwardly and forwardly toward and away from each end of said housing and having a portion engageable with each tube when said clamp member overlies said tube at a place in which it is supported by said support surface, said clamp member being guided in said housing so that it is brought close enough to said support surface to compress the tube and at least reduce the flow therethrough, and guide means in said housing for guiding said clamp member for said backward and forward movement, said tube support surface in at least one of said channels is offset from said support surface of at least one of the other of said channels so that when said clamp member is positioned to close off at least a portion of the flow through one of the tubes it is located so that it does not effect the closing off of the cross-section of at least one of the other of said tubes, said clamp member being positionable in at least one position wherein at least one of said tubes is clamped off, in another position wherein at least two of said tubes are open and in a further position in which at least two of said tubes are shut off.

2. A multiway valve according to claim 1, wherein said housing includes two substantially parallel channels, one of said channels having a support surface offset from the other of said channels, said clamp member comprising a single member movable in a path overlying both of said channels and substantially parallel to said tube support surfaces of said channels.

3. A multiway valve according to claim 2, wherein said clamping member comprises a roller having journals on each side, said guide means comprising a groove in each side of said housing in which the respective journals are guided.

4. A multiway valve according to claim 1, wherein at least one of said two support surfaces include a recess therein into which a tube may be displaced by said clamp member.

5. A multiway valve according to claim 1, wherein said housing includes first and second substantially parallel channels, one of said channels having a support surface which extends from said rear end inwardly but not beyond the center of said housing, the second channel having a support surface defined only in a central portion of said second channel.

6. A multiway valve according to claim 1, wherein said clamp member comprises a plurality of separate clamping surfaces.

7. A multiway valve comprising a housing having first and second substantially parallel channels extending therethrough, one of said channels having a support surface extending inwardly from one end, the other of said channels having a support surface located centrally therein including a portion which is alongside a portion of the surface in the first of said channels, a guide groove defined in said housing at a location above said support surfaces, a roller having a journal extending outwardly from each side engaged in a respective guide groove on a respective side of said housing and including a periphery being movable upon rotation of said roller from one end of said housing to the opposite end and having a periphery which comes into close proximity with the respective support surfaces in each of said channels so that a tube positioned on the support surfaces will be closed off at least partially by movement of the said roller along said housing, each of said first and second channels having areas along its length other than said support surface areas which permit deflection of a tube positioned therein out of the way of said roller so that said roller does not compress a tube therein, said first and second channel support surfaces and said roller being of a construction so that in a respective first position of said roller at least one of said tubes is clamped off, in a second position where both of said tubes are open and in a third position where both of said tubes are shut off by said roller.

8. A multiway valve according to claim 7, wherein at least one of said channel support surfaces includes a groove therein having a cross-section diminishing along the longitudinal length of said support surface.

9. A multiway valve according to claim 8, wherein the groove of said support surface extends at an angle to said support surface.

10. A multiway valve according to claim 8, wherein said support surfaces of each of said channels includes a groove having a varying width and depth.

11. A multiway valve according to claim 8, wherein said roller comprises a cylindrical roller having a periphery engageable with a tube positioned over the support surfaces in respective ones of said first and second channels.

* * * * *